United States Patent [19]

Keeley

[11] 4,268,647

[45] May 19, 1981

[54] ORGANIC MATERIALS HAVING META, PARA-ISOPROPYLIDENE DIPHENOXY UNITS AND METHOD

[75] Inventor: Donald E. Keeley, Menlo Park, Calif.

[73] Assignee: General Electric Company, Schenectady, N.Y.

[21] Appl. No.: 151,389

[22] Filed: May 19, 1980

Related U.S. Application Data

[62] Division of Ser. No. 966,896, Dec. 6, 1978.

[51] Int. Cl.³ .................. C08G 8/20; C08G 63/18; C08G 65/22
[52] U.S. Cl. ...................... 525/474; 528/170; 528/171; 528/176; 528/196; 528/219; 528/211; 528/87
[58] Field of Search ............ 525/474; 528/170, 171, 528/176, 196, 211, 219, 87

[56] References Cited

U.S. PATENT DOCUMENTS

| | | | |
|---|---|---|---|
| 3,014,891 | 12/1961 | Goldblum | 528/196 |
| 3,021,305 | 2/1962 | Goldberg | 528/196 |
| 3,030,335 | 4/1962 | Goldberg | 528/196 |
| 3,510,415 | 5/1970 | Barth | 528/219 |

FOREIGN PATENT DOCUMENTS

| | | | |
|---|---|---|---|
| 2027610 | 12/1971 | Fed. Rep. of Germany . | |
| 1960747 | 8/1973 | Fed. Rep. of Germany . | |
| 49-20562 | 5/1974 | Japan . | |
| 987794 | 3/1965 | United Kingdom | 528/196 |
| 1074398 | 7/1967 | United Kingdom | 528/196 |
| 1425773 | 2/1976 | United Kingdom | 528/219 |

*Primary Examiner*—Wilbert J. Briggs, Sr.
*Attorney, Agent, or Firm*—William A. Teoli; James C. Davis, Jr.

[57] ABSTRACT

Meta,para-isopropylidene bisphenol is homopolymerized and copolymerized to produce a variety of high performance thermoplastics having improved processing characteristics. In addition to polycarbonates, there are provided polyesters, polyestercarbonates, polyepoxides, polysulfones, polyetherimides, polyformals, epoxy resins and polycarbonate-polydiorganosiloxane block polymers.

10 Claims, No Drawings

ORGANIC MATERIALS HAVING META, PARA-ISOPROPYLIDENE DIPHENOXY UNITS AND METHOD

This is a division, of application Ser. No. 966,896, filed Dec. 6, 1978.

BACKGROUND OF THE INVENTION

Polycarbonates have been used in a wide variety of applications requiring high performance thermoplastic materials. Although polycarbonates consisting essentially of chemically combined units of the formula,

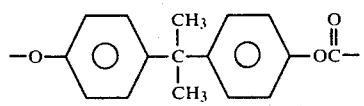

has been satisfactorily molded at temperatures exceeding 250° C., or injection molded to plastic foams at temperatures exceeding 300° C. using particular blowing agents, the use of such polycarbonates, or the employment of additional blowing agents has been somewhat restricted due to the high temperature polycarbonate shaping requirements. It is also known, for example, that polycarbonate consisting essentially of chemically combined units of formula (1) has a glass transition temperature of 150° C. while the corresponding polycarbonate derived from ortho,para-bisphenol-A has a glass transition temperature of 142° C. Continued efforts have been made by the organic thermoplastics industry to improve the flow characteristics of polycarbonates and other organic thermoplastics having chemically combined isopropylidene bisphenol units.

STATEMENT OF THE INVENTION

In my copending application Ser. No. 966,895, filed Dec. 6, 1978 and assigned to the same assignee as the present invention, there is shown meta,para-isopropylidene bisphenol of the formula

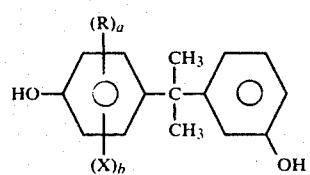

where R is selected from the class consisting of $C_{(1-8)}$ alkyl radicals, $C_{(1-6)}$ alkoxy radicals, X is selected from halogen, a is a whole number equal to 0 to 4 inclusive, b is a whole number equal to 0 to 3 inclusive and the sum of a and b is equal to 0 to 4 inclusive.

I have found that meta,para-isopropylidene bisphenol included within the scope of formula (2) can be polymerized to a polycarbonate having an $M_w$ of 72,175, an $M_n$ of 13,380 and a glass transition temperature of 112° C.

DESCRIPTION OF THE INVENTION

There is provided by the present invention, a method for making polycarbonates having at least three mole percent of chemically combined bisphenol units of the formula,

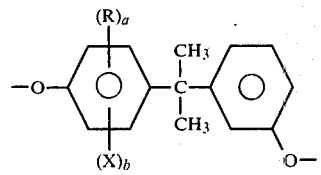

based on the total moles of chemically combined bisphenol units, which comprises, (A) phosgenating a mixture comprising from 3 to 100 mole percent of a bisphenol of formula (2) and from 0 to 97 mole percent of a bisphenol of the formula,

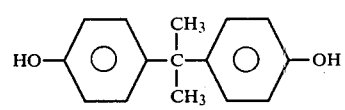

to produce a polycarbonate, and (B) effecting the separation of the polycarbonate from the mixture of (A), where R, X a and b are as previously defined.

Bisphenols included by formula (3) are, for example,

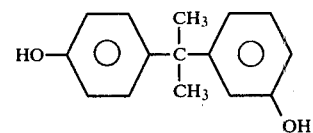

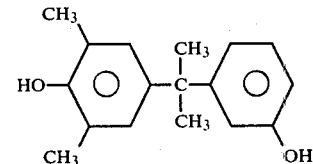

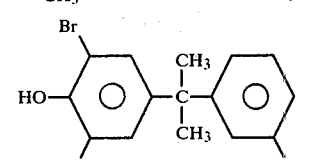

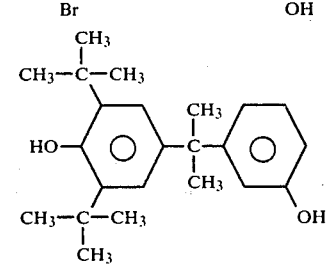

In a further aspect of the present invention, there are provided aromatic polyformals consisting essentially of

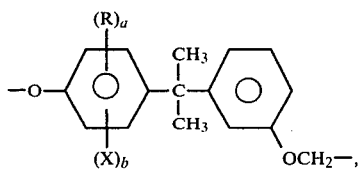

chemically combined with 0 mole percent to 97 mole percent of units of the formula,

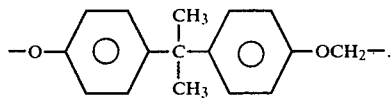

In addition, there are provided aromatic polysulfones consisting essentially of chemically combined units of the formula,

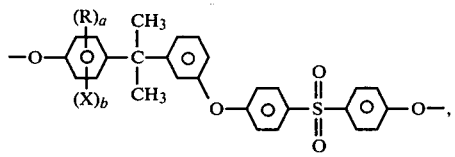

where R, X, a and b are as previously defined.

Another aspect of the present invention is directed to aromatic polyesters consisting essentially of chemically combined units of the formula,

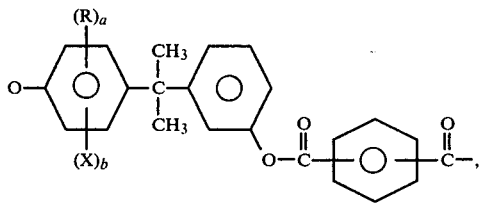

where R, X, a and b are as previously defined.

An additional aspect of the present invention is directed to bisimides of the formula,

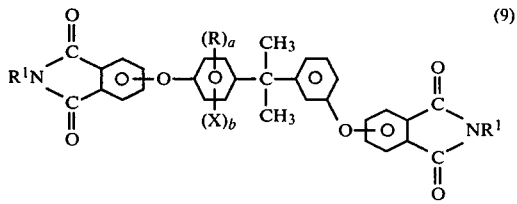

where R, X, a and b are as previously defined and $R^1$ is selected from $C_{(1-8)}$ alkyl radicals and $C_{(6-12)}$ aryl radicals.

The bisimides of formula (9) can be made by the procedure of Heath et al U.S. Pat. No. 3,879,428, assigned to the same assignee as the present invention. A nitro phthalimide

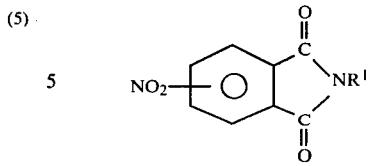

can reacted with a bisphenoxide of the formula,

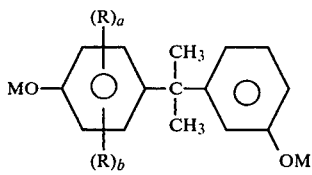

to produce a bisimide within formula (8), where R, X, $R^1$, a and b are as previously defined and M is an alkali metal ion such as sodium.

The bisimide of formula (9) can thereafter be hydrolyzed to produce the dianhydride of the formula,

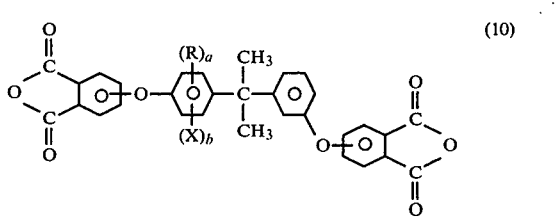

where R, X, a and b are as previously defined. Polyetherimides also can be made from the dianhydride by a melt polymerization procedure, or an organic solvent solution polymerization with an organic diamine of the formula, $NH_2R^2NH_2$, in accordance with Takekoshi et al U.S. Pat. Nos. 3,803,085 and 3,991,004, where $R^2$ is a divalent organo radical selected from the class consisting of (a) aromatic hydrocarbon radicals having from 6–20 carbon atoms and halogenated derivatives thereof, (b) alkylene radicals, $C_{(2-8)}$ alkylene terminated polydiorganosiloxane cycloalkylene radicals having from 2–20 carbon atoms, and (c) divalent radicals included by the formula,

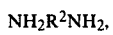

where Q is a member selected from the class consisting of

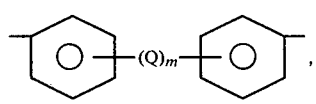

—$C_xH_{2x}$— and x is a whole number from 1 to 5 inclusive, and m is 0 or 1.

The polyetherimides of the present invention consist essentially of chemically combined units of the formula,

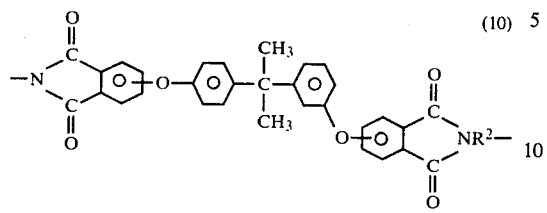

(10)

where R, X, a, b and $R^2$ are as previously defined.

In addition to para,para-bisphenol of formula (4), the meta,para-bisphenol of formula (2) also can be copolymerized with 1,1-dichloro-2,2-bis(4-hydroxyphenyl)ethylene. The meta,para-bisphenol of formula (2) or mixtures thereof with p,p-bisphenol-A also can be used to make polycarbonate-organopolysiloxane block polymers by effecting reaction in the presence of an acid acceptor between one or more moles of the m,p-bisphenol of formula (2) and a chlorine chain-stopped polydiorganosiloxane of the formula,

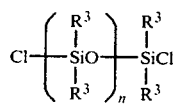

where $R^3$ is a monovalent organic radical selected from methyl, ethyl, propyl, vinyl, phenyl, chlorophenyl, perfluoropropyl, cyanoethyl and mixtures thereof and n has an average value of 5–200 inclusive. A typical procedure is shown by Vaughn U.S. Pat. No. 3,189,602, assigned to the same assignee as the present invention.

The above aromatic organic polymeric materials can have an intrinsic viscosity in methylene chloride at 25° C. of at least 0.1 and preferably at least 0.3 and are selected from polycarbonates consisting essentially of formula (3) units, copolymers consisting essentially of formula (1) and (3) units, polyesters, polyestercarbonates, polyformals, polyetherimides, polysulfones and polycarbonate-polydiorganosiloxane block polymers, etc. The organic polymeric materials can have at least 3 mole percent to 100 mole percent of chemically combined units of formula (3) and preferably from 10 to 100 mole percent of such units. These organic polymeric materials can be injection molded to a variety of shapes, transformed into high performance shaped foams, used in forming plastic sheets, laminates, etc. The organic polymers having chemically combined formula (3) units have improved processing characteristics and can be reinforced with various particulated fillers such as glass fibers, silica fillers, carbon whiskers, up to 50 percent by weight of the resulting total blend. Reinforcement of polymer can be accomplished prior to polymer formation by effecting polymerization in the presence of filler. Melt blending and solution blending also can be employed.

In order that those skilled in the art will be better able to practice the invention, the following examples are given by way of illustration and not by way of limitation. All parts are by weight.

EXAMPLE 1

A mixture of 5 parts of phenol, 1 part of meta-isopropenyl phenol and about 21 parts of toluene was added dropwise to about 5 parts of a 75% aqueous solution of sulfuric acid. When the addition was completed, the reaction mixture was stirred an additional 5 minutes, diluted with about 35 parts of diethylether resulting in the separation of 2 layers. The organic layer was washed with about 25 parts of a saturated aqueous sodium bicarbonate solution, dried over magnesium sulfate and concentrated under reduced pressure. There was obtained a brown oil which was crystallized from chloroform resulting in an 81% yield of a white powder having a melting point of 97°–98° C. Based on method of preparation and its IR spectrum, the product was meta,para-isopropylidene bisphenol of the formula,

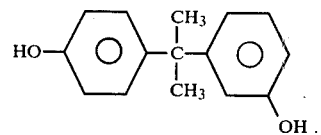

Phosgene was introduced into a mixture over a 20 minute period of 2 parts of the above meta,para-bisphenol, 22 parts of methylene chloride, about 7 parts of water, about 0.04 part of triethylamine and 0.016 part of phenol. There was added a total of 0.9 part of phosgene while the mixture was agitated along with a sufficient amount of an aqueous sodium hydroxide solution to maintain the reaction mixture at a pH of 10–12. After the phosgene addition, the mixture was flushed with nitrogen and washed once with about 25 parts of a 10% hydrochloric acid solution. The mixture was then blended with about 100 parts of methanol resulting in the precipitation of product. The product was recovered by vacuum filtration and dried under vacuum at 65° C. for 18 hours. Based on method of preparation the product was a polycarbonate consisting essentially of chemically combined units of the formula,

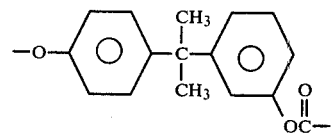

and chain terminated with phenoxy units. The product was found to be a valuable injection moldable thermoplastic material having a glass transition temperature of about 112° C. Those skilled in the art know that the polycarbonate has improved processing characteristics as compared to para,para-isopropylidene bisphenol polycarbonate having a glass transition temperature of about 150° C.

EXAMPLE 2

A mixture of 3.5 parts of the meta,para-bisphenol-A of Example 1, 3.5 parts of para,para-bisphenol-A, 16 parts of water, about 26 parts of methylene chloride, about 0.03 part of triethylamine, and 0.072 part of phenol was phosgenated over a 20 minute period. During phosgenation 3.4 parts of phosgene was introduced and sufficient 20% aqueous sodium hydroxide solution to maintain the reaction mixture at a pH in the range of 10–11.5. After phosgenation, the organic layer was separated from the mixture and added dropwise to about 240 parts of methanol in a blender. There was obtained a precipitated polymer which was recovered by vacuum filtration and redissolved in methylene chloride and reprecipitated from methanol. Based on method of preparation, the product was a copolymer consisting essentially of meta,para-isopropylidene bisphenoxy units chemically combined with para,para-isopropylidene bisphenoxy units which were present in about equal molar amounts. The polymer had an $M_w$ of 29,204, an $M_n$ of 10,785 and a $T_g$ of 130° C. Those skilled in the art would know that the processing characteristics of the aforementioned copolymer with respect to its ability to be molded to various parts would be superior to a polycarbonate consisting essentially of chemically combined para,para-isopropylidene bisphenoxy units having a glass transition temperature of 150° C.

EXAMPLE 3

There was added with stirring 1.7 part of sodium hydroxide to a mixture of 4.54 parts of meta,para-bisphenol-A, 0.0459 part of 4-t-butyl phenol, about 8.2 parts of methylene chloride and about 10.2 parts of N-methylpyrrolidone. The reaction mixture was refluxed for 5 hours at 90° C. The reaction mixture was then cooled slightly and poured into about 120 parts of methanol in a blender. The product which precipitated was collected by vacuum filtration, dissolved in about 20 parts of methylene chloride and reprecipitated with about 120 parts of methanol followed by drying at 70° C. under vacuum for 16 hours. There was obtained a polyformal having an $M_w$ of 49,700, an $M_n$ of about 15,560 and a glass transition temperature of 55° C. The polyformal was found to be a valuable thermoplastic injection moldable material reinforceable with a variety of inert materials and useful in a variety of applications, such as for organic solvent resistant wire coating formulations.

EXAMPLE 4

A mixture of 7 parts of meta,para-bisphenol-A, 16.6 parts of dimethylsulfoxide and 45 parts of chlorobenzene was stirred and heated to 70° C. to produce a clear solution. Nitrogen was then bubbled into the mixture and about 3.2 parts of a 50% aqueous sodium hydroxide solution was added during a 5 minute period resulting in a ratio of about 2 moles of sodium hydroxide per mole of the meta,para-bisphenol-A. The mixture was then brought to reflux and the solvent was distilled from the mixture until the pot temperature reached a 160° C. There was then added a 50% solution of 8.81 parts of 4,4'-dichlorodiphenylsulfone and chlorobenzene at such a rate to maintain the temperature of the mixture at least 150° C. The resulting mixture had an equal molar amount of sulfone and bisphenol and the stirring of the mixture continued for 2 hours at 150°–160° C. The polymerization was terminated by passing methyl chloride gas into the mixture until it faded to a light amber color. The mixture was then cooled to room temperature and diluted with 133 parts of methylene chloride and precipitated twice from methanol. Based on method of preparation there was obtained a polysulfone having an $M_w$ or 49,153, an $M_n$ of 23,293 and a glass transition temperature of 142° C. It was found that the corresponding polysulfone having chemically combined para,para-isopropylidene bisphenol units has a glass transition temperature of 190° C. Those skilled in the art would know that the polysulfone made in accordance with the practice of the present invention has improved processing characteristics and convertible to a variety of high performance shapes and parts by standard injection molding techniques.

EXAMPLE 5

Phosgene is introduced into a mixture at a rate of 3.5 parts of phosgene per hour consisting of 77.75 parts of meta,para-bisphenol-A, 136.9 parts of a bisphenol-A terminated polydimethylsiloxane having an average of 15 dimethylsiloxy units, 330 parts of chloroform, 0.6 part of phenol, 0.9 part of sodium gluconate, 2.14 parts of triethylamine and 1400 parts of water. During the phosgenation, aqueous sodium hydroxide is added to the mixture to maintain a pH of about 11.

After the mixture is stirred for 27 minutes, the phosgene flow rate is reduced to about 1 part per minute and continued until the entire amount of base is consumed, which includes 144 parts of sodium hydroxide added as an aqueous mixture. The total reaction time is 111 minutes. Nitrogen is then bubbled into the two phase mixture to remove any residual phosgene. The reaction mixture is then diluted with an equal volume of chloroform and the aqueous layer is separated and discarded. The organic layer is washed with deionized water having a pH of 6.7 and aqueous HCL having a pH of 2.0 and thereafter four times with deionized water. The organic layer is washed with additional water until it is chloride free, based on a silver nitrate test. The organic layer is then dried over magnesium sulfate and filtered. The resulting clear solution is then added over a 30 minute period to a well stirred mixture of acetone and methanol to effect the precipitation of product. There is obtained a fibrous polymer which is filtered and pressed dry and then washed with additional acetone-methanol solution and refiltered. Based on method of preparation, there is obtained a block polymer containing about 30% by weight of dimethylpolysiloxane and about 70% by weight of polycarbonate. The block polymer is useful as for making semi permeable membranes.

EXAMPLE 6

A mixture of 20.52 parts of meta,para-bisphenol-A, 38.97 parts of 4-nitro,N-methylphthalimide, 7.92 parts of sodium hydroxide, 101 parts of dimethylformamide and 58.5 parts of toluene is heated at reflux under a nitrogen atmosphere. The pot temperature during this period is 125° C. The mixture is heated for 6 hours and then refluxed for an additional two hours and allowed to cool to 100° C. Toluene is then removed under reduced pressure and the mixture is allowed to cool to room temperature. There is obtained a precipitate. The mixture is then diluted with about 300 parts of ethanol and filtered. There is obtained a white solid after the precipitate is washed with water and dried. The yield of product is about 90%. Based on method of the preparation the product is a bisimide of the formula,

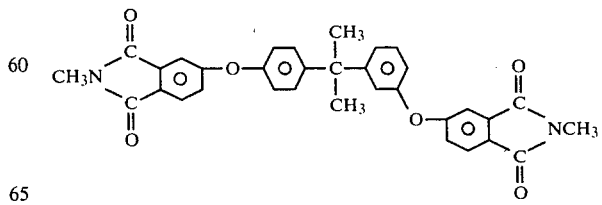

A mixture of 93 parts of the above bisimide and 52.25 parts of sodium hydroxide, and 260 parts of water is heated to reflux. Methylamine is distilled along with water at a rate of about 80 parts per hour and fresh water is added to the mixture. A mixture is heated for a total of 20 hours and the mixture is allowed to cool slowly. There is obtained a solid which is isolated by filtration in a centrifuge. Based on method of preparation there is formed tetra-acid having the formula,

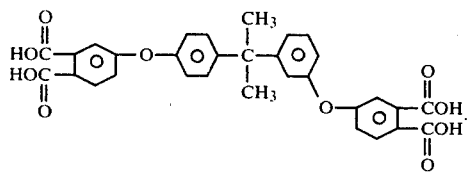

A mixture of 45 parts of the above tetra-acid, 30 parts of acetic anhydride and 217 parts of toluene is heated to reflux and held at reflux for 1 hour. The filtrate is allowed to cool slowly. There is obtained a crystalline dianhydride having the following formula,

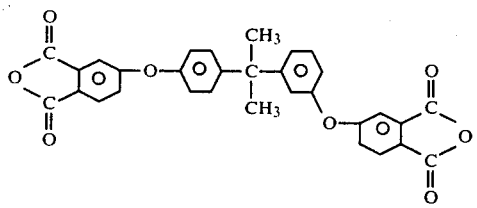

EXAMPLE 7

A mixture of 5.0205 parts of meta,para-bisphenol-A dianhydride of Example 6, 1.47 part of metaphenylenediamine and 0.089 part of phthalic anhydride is stirred and heated under a nitrogen atmosphere. The resulting viscous melt is further heated at 280° C. for 1 hour. There is obtained upon cooling a tough clear amber colored material. Based on method of preparation the product is a polyetherimide consisting essentially of chemically combined units of the formula,

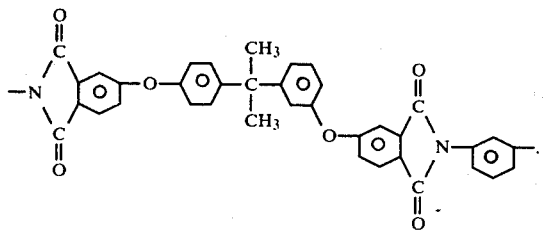

The above polyetherimide is injection molded to a finished shape resulting in a tough solvent resistant structure.

EXAMPLE 8

A mixture is phosgenated consisting of 3.5 parts of m,p-bisphenol-A, 4.31 parts of 1,1-dichloro-2,2-bis(4-hydroxy phenyl)ethylene, 16 parts of water, 39 parts of methylene chloride, 0.040 part of triethylamine and 0.027 part of phenol. There is added 3.4 parts of phosgene and sufficient 20% aqueous sodium hydroxide solution during the 20 minute phosgenation period to maintain the pH of the mixture in the range of 10–11.5. The reaction mixture is then allowed to separate into 2 layers and the organic layer is added dropwise to about 250 parts of methanol while it is rapidly agitating. There is obtained a precipitated product which is collected by vacuum filtration. Based on method of preparation the product is a polycarbonate copolymer consisting essentially of chemically combined units of the formula,

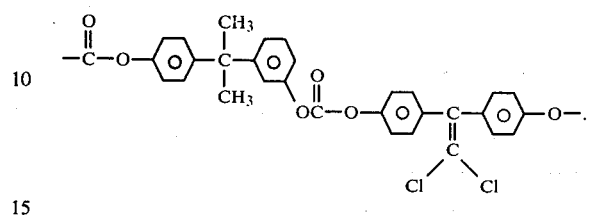

A solution of the above copolymer in methylene chloride is cast onto a glass plate. The resulting film is found to be a tough thermoplastic exhibiting flame retardant properties.

EXAMPLE 9

There was added a solution of 3 parts of sodium laurylsulfate in 12 parts of water to a solution while it was stirred of 4.56 parts of meta,para-bisphenol-A and 1.6 part of sodium hydroxide in 120 parts of water. There was then added to the resulting mixture a solution of 4.06 parts of terephthaloyl chloride in about 90 parts of chloroform. An emulsion was formed from the resulting mixture which was stirred an additional 5 minutes. The reaction mixture was then poured into 500 parts of acetone to effect the precipitation of product which was collected and washed well with water. The product was then reprecipitated. There was obtained a polyester having a glass transition temperature of 150° C., an $M_w$ of 54,834 and an $M_n$ of 36,999. Based on method of preparation the product consists essentially of chemically combined units of the formula,

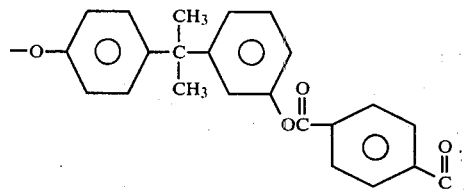

The above polyester is found to be injection moldable and convertible to a high strength material.

Although the above examples are directed to only a few of the very many thermoplastic organic materials which can be made in accordance with the practice of the present invention, it should be understood that the present invention is directed to a much broader variety of thermoplastic materials based on the use of bisphenols of formula (2) alone or in combination with various other materials which are described in the specification preceding these examples. Included are, for example, epoxy resins consisting essentially of units derived from the diglycidyl ether of meta,para-isopropylidene bisphenol.

What I claim as new and desire to secure by Letters Patent of the United States is:

1. Thermoplastic organic polymers having chemically combined units of the formula,

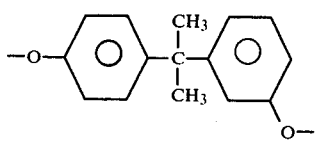

which are selected from the class consisting of polyestercarbonate copolymers, polyesters, polyformals, polysulfones, polyetherimides and organopolysiloxane-polycarbonate block polymers.

2. A thermoplastic organic polymer in accordance with claim 1 consisting essentially of meta,para-isopropylidene bisphenoxy units and formal units.

3. A thermoplastic organic polymer in accordance with claim 1, consisting essentially of meta,para-isopropylidene bisphenoxy units and diphenylsulfone units.

4. A thermoplastic organic polymer in accordance with claim 1, consisting essentially of meta,para-isopropylidene bisphenoxy units and organosiloxy units.

5. A thermoplastic polyetherimide in accordance with claim 1, consisting essentially of chemically combined units of the formula,

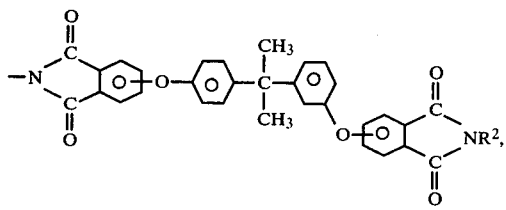

where $R^2$ is a divalent organo radical selected from the class consisting of (a) aromatic hydrocarbon radicals having from 6–20 carbon atoms and halogenated derivatives thereof, (b) alkylene radicals, $C_{(2-8)}$ alkylene terminated polydiorganosiloxane cycloalkylene radicals having from 2–20 carbon atoms, and (c) divalent radicals included by the formula,

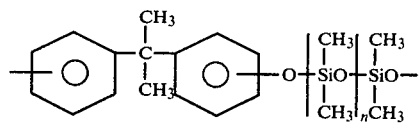

where Q is a member selected from the class consisting of $$-O-, -\overset{O}{\underset{\|}{C}}-, -\overset{O}{\underset{\underset{\|}{O}}{\overset{\|}{S}}}-, -S-,$$

$-C_xH_{2x}$, x is a whole number from 1 to 5 inclusive, and m is 0 or 1.

6. A thermoplastic organic polymer in accordance with claim 1, consisting essentially of meta,para-isopropylidene bisphenoxy units and dimethylsiloxy units.

7. A thermoplastic organic polymer in accordance with claim 1, consisting essentially of meta,para-isopropylidene bisphenoly units chemically combined with units of the formula, $$-O-\underset{}{\underset{}{\bigcirc}}-\underset{\underset{Cl}{\overset{C}{|}}}{\overset{\underset{}{C}}{|}}-\underset{}{\underset{}{\bigcirc}}-O-$$

8. A thermoplastic organic polymer in accordance with claim 1, consisting essentially of meta,para-isopropylidene bisphenoxy units chemically combined with units of the formula, $$-\bigcirc-\underset{CH_3}{\overset{CH_3}{\underset{|}{\overset{|}{C}}}}-\bigcirc-O-[\underset{CH_3}{\overset{CH_3}{\underset{|}{\overset{|}{Si}O}}}-\underset{CH_3}{\overset{CH_3}{\underset{|}{\overset{|}{Si}O}}}-]_n$$

where n has an average value of 5 to 200.

9. A thermoplastic organic polymer in accordance with claim 1, consisting essentially of meta,para-isopropylidene bisphenoxy units chemically combined with dicarboxyphenylene units.

10. An organic polymer consisting essentially of chemically combined diglycidyl ether units of meta,-para-isopropylidene bisphenol.

* * * * *